United States Patent [19]

Kárpáti et al.

[11] 4,048,322
[45] Sept. 13, 1977

[54] BRONCHIALLY EFFECTIVE XANTHENE-9-CARBOXYLATES

[75] Inventors: Egon Kárpáti; László Szporny both of Budapest; Mihaly Bartók, Szeged; József Czombos, Szeged; Károly Felfoldi, Szeged; Marta Laszlavik, Szeged; Ferenc Notheisz, Szeged, all of Hungary

[73] Assignee: Richter Gedeon Vegyeszeti Gyar R.T., Budapest, Hungary

[21] Appl. No.: 673,135

[22] Filed: Apr. 2, 1976

[30] Foreign Application Priority Data

June 27, 1975 Hungary ............... RI 569

[51] Int. Cl.$^2$ ............................ C07D 311/84
[52] U.S. Cl. ....................... 424/283; 260/335; 424/274; 260/326.36
[58] Field of Search ............... 260/335; 424/283

[56] References Cited

U.S. PATENT DOCUMENTS

| | | | |
|---|---|---|---|
| 2,334,310 | 11/1943 | Burtner | 260/335 |
| 2,512,307 | 6/1950 | Clinton et al. | 260/335 |
| 2,659,725 | 11/1953 | Cusic et al. | 260/335 |
| 2,659,732 | 11/1953 | Cusic et al. | 260/335 |
| 3,133,937 | 5/1964 | Davis | 260/335 |

OTHER PUBLICATIONS

J. W. Cusic et al., Jour. Org. Chem., vol. 16, (1951), pp. 1921-1930.

*Primary Examiner*—Norma S. Milestone
*Attorney, Agent, or Firm*—Karl F. Ross

[57] ABSTRACT

The invention relates to new xanthene-9-carboxylates of the formula (I),

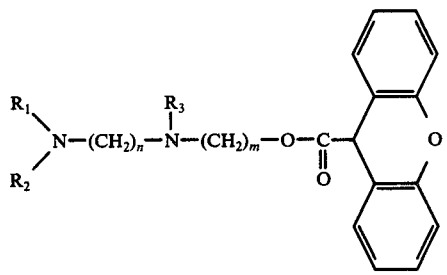

wherein
$R_1$ and $R_3$ are the same or different and each can represent a lower alkyl group,
$R_2$ is a lower alkyl group or a group of the formula (VI),

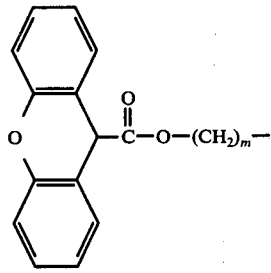

wherein m is an integer of 2 to 5, or
$R_1$ and $R_2$ form, together with the adjacent nitrogen atom, a five- or six-membered heterocyclic group, and $n$ and $m$ each represent integers of 2 to 5, or salts thereof. These compounds possess cholinolytic and bronchospasmolytic effects and are completely devoid of harmful side-effects. Thus these compounds can be used to great advantage in therapy. The new compounds of the formula (I) or their salts can be prepared by reacting a diaminoalcohol of the formula (III),

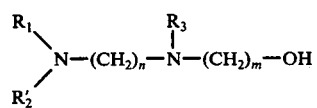

wherein $R_2'$ is lower alkyl or a group of formula -(CH$_2$)$_m$-OH, with a reactive derivative of xanthene-9-carboxylic acid, and, if desired, converting the obtained product into its salt.

9 Claims, No Drawings

BRONCHIALLY EFFECTIVE XANTHENE-9-CARBOXYLATES

This invention relates to new xanthene-9-carboxylates which can be incorporated into pharmaceutical compositions.

More particularly, the invention relates to new xanthene-9-carboxylates having the formula (I) and salts thereof,

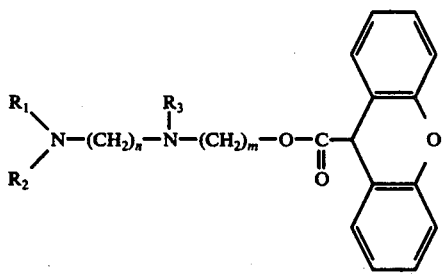
(I)

wherein
$R_1$ and $R_3$ are the same or different and can each be lower alkyl,
$R_2$ is lower alkyl group or a group of the formula (VI),

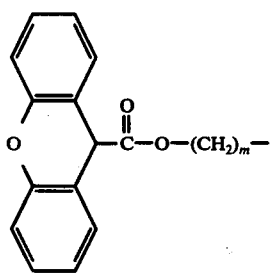
(VI)

wherein $m$ is an integer of 2 to 5, or
$R_1$ and $R_2$ form, together with the adjacent nitrogen atom, a five- or six-membered heterocyclic group, and
$n$ and $m$ each represent integers of 2 to 5.

The salts of the compounds having the formula (I) may be pharmaceutically acceptable acid addition salts or quaternary salts. These salts correspond to the formula (II),

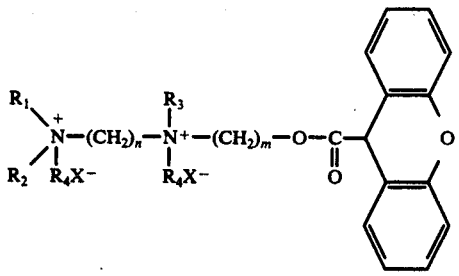
(II)

wherein $R_1$, $R_2$, $R_3$, $m$ and $n$ each have the same meanings as defined above, $R_4$ is hydrogen or, and X is an organic or mineral acid residue.

When $R_1$, $R_2$, $R_3$ and $R_4$ are lower alkyl, they can represent $C_{1-6}$, particularly $C_{1-4}$ alkyl groups, such as methyl, ethyl, propyl, isopropyl, butyl, isobutyl, sec-butyl or tert-butyl. The most preferred alkyl groups are methyl and ethyl. When $R_1$ and $R_2$ form, together with the adjacent nitrogen atom, a five- or six-membered heterocyclic group, this group is preferably a saturated ring, particularly a pyrrolidine group.

In the above and subsequent formulae $m$ and $n$ each can be an integer of 2 to 5, preferably 2 or 3, thus the two nitrogen atoms, and one of the nitrogen atoms and the carboxylic oxygen, respectively, are connected with each other through an ethylene, n-propylene or n-butylene group, particularly an n-propylene group.

When $R_2$ is a group of the formula (VI), it can be xanthene-9-carbonyloxy-lower alkyl, wherein $m$ is preferably 2 or 3. The most preferred of these groups is 3-(xanthene-9-carbonyloxy)-propyl.

Particularly preferred are those compounds of the formula (I) in which $R_1$ is methyl or ethyl, $R_2$ is methyl or ethyl, $R_3$ is methyl, and $n$ and $m$ each are 2 or 3. In the most preferred representative of these compounds, $R_1$ and $R_2$ are ethyl, $R_3$ is methyl, and $n$ and $m$ are each to 3.

The compounds of the formula (II) in which $R_4$ is hydrogen are the acid addition salts of the bases having the formula (I), whereas the compounds containing a lower alkyl group as substituent $R_4$ are quaternary salts.

In accordance with the invention, the new xanthene-9-carboxylates can be prepared by reacting a diaminoalcohol of the formula (III)

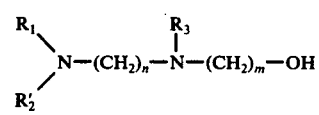
(III)

wherein $R_2'$ is a lower alkyl or a group of the formula $—(CH_2)_m—OH$, with a reactive derivative of xanthene-9-carboxylic acid.

The reaction is performed preferably by esterifying a compound of the formula (IV),

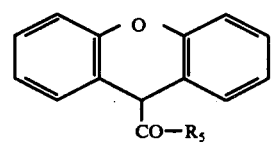
(IV)

wherein $R_5$ is a halogen, preferably chlorine, or a lower alkoxy, preferably methoxy or ethoxy, with an alcohol of the formula (III).

The reaction can be carried out in an inert organic solvent, such as in an anhydrous halogenated aliphatic hydrocarbon, e.g. chloroform or carbon tetrachloride, or in an aromatic solvent, e.g. benzene, toluene, xylene, preferably benzene. When the starting substance is a compound of the formula (IV) in which $R_5$ is lower alkoxy, the reaction can also be performed in the absence of solvent under anhydrous conditions. In this instance it is preferred to add a catalytic amount of an alkali metal alcoholate, such as sodium or potassium methoxide or ethoxide, to the reaction mixture. The reaction temperature may vary within wide limits, e.g. between 40° and 150° C. It is preferred, however, to perform the reaction at the boiling point of the system or at about 100° C under refluxing conditions. The alkanol which can be formed in the reaction, can be removed by distillation. The reaction time depends on the reaction conditions applied, and may vary e.g. between 0.5 and 6 hours.

The compound of the formula (IV) is preferably used preferably in a slight excess, such as in an amount of 1.05 to 1.2 moles per one mole of the alcohol of the formula (III). When a compound of the formula (I) containing as $R_2$ a group of the formula (VI) is to be prepared, or when the starting substance is a compound of the formula (IV) in which $R_5$ is alkoxy the molar ratio of the compounds having the formulae (IV) and (III) must be at least 2:1.

The reaction can be performed by dissolving an acid halide in an anhydrous solvent, adding a solution of the appropriate diaminoalcohol in an anhydrous inert solvent dropwise to the above solution under cooling, and then refluxing the reaction mixture obtained. When the reaction has ceased, the mixture is cooled, rendered alkaline with an aqueous alkali hydroxide solution (e.g. aqueous sodium hydroxide solution), the organic phase is separated, and dried, and the solvent is evaporated.

According to another method, a solution of an alkali alcoholate is added to the heated mixture of the starting substances, the reaction mixture is heated at about 100° C, and the alcohol product is removed simultaneously. When the reaction has terminated, the mixture is cooled, dissolved in an organic solvent, and admixed with a dilute aqueous solution of a mineral acid. The solution is decolorized, dried, rendered alkaline, and extracted, e.g. with ether, if necessary. The resulting ethereal solution is dried, and the solvent is evaporated.

The obtained compound of the formula (I) can be separated and purified according to methods known per se, or optionally these compounds can be converted directly, i.e., without separation, into the acid addition salts or quaternary salts of the general formula (II).

The acid addition salts are prepared by contacting the free base with mineral or organic acids, such as hydrogen halides (e.g. hydrochloric, hydrobromic or hydroiodic acid), or sulfuric acid, phosphoric acid, acetic acid, propionic acid, butyric acid, maleic acid, fumaric acid, citric acid, malic acid, tartaric acid, etc.

The quaternary salts are prepared by contacting the free base with a compound of the formula (V), $$R_4 - X \quad \quad (V)$$

The most preferred reagents for forming quaternary salts are the lower alkyl halides, but other alkyl compounds capable of forming quaternary salts can be used as well. The only provision is that the anion should be physiologically and pharmacologically acceptable.

The quaternary salts can be prepared according to known methods, such as by dissolving the free base in an organic solvent, adding the quaternarizing agent (e.g. an alkyl halide) to the solution, heating the mixture gently, and then allowing it to stand under cooling. The separated crystals are filtered off, washed, dried, and recrystallized, if necessary.

The starting compounds of the formula (III) can be prepared as follows:

a. To prepare a compound of the formula (III) in which $n$ is equal to 3, a secondary amine of the general formula (VII),

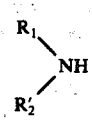

(VII)

is reacted with an acrylate of the formula (VIII), $$CH_2=CH-\overset{\overset{\displaystyle O}{\|}}{C}-OR \quad \quad (VIII)$$

wherein R is lower alkyl; the resulting aminopropionate of the general formula (IX)

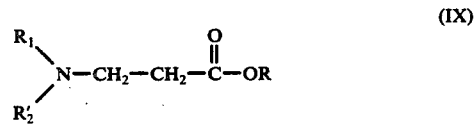

(IX)

is reacted with an amine of the general formula (X), $$R_3 - NH_2 \quad \quad (X)$$

The resulting aminopropionic amide of the formula (XI)

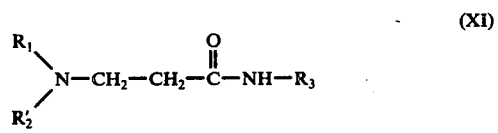

(XI)

is reduced, and finally, the resulting diamine of the formula (XII)

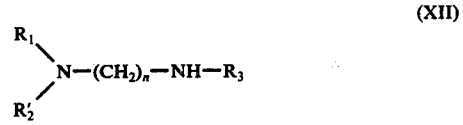

(XII)

wherein $n$ is equal to 3, is reacted with a haloalcohol of the formula (XIII), $$Hal-(CH_2)_m-OH \quad \quad (XIII)$$

wherein Hal stands for halogen.

b. A secondary amine of the general formula (VII) is reacted with a haloalcohol of the formula (XIX)

$$Hal-(CH_2)_n-OH \quad \quad (XIX)$$

wherein Hal stands for halogen and $n$ is an integer from 2 to 5. The obtained aminoalcohol of the formula (XIV),

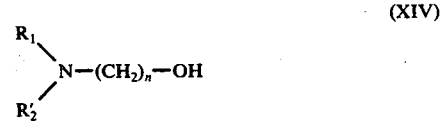

(XIV)

is reacted with thionyl chloride, and the resulting aminoalkyl chloride of the formula (XV)

(XV)

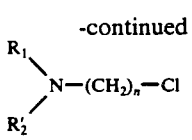

is reacted with an aminoalcohol of the formula (XVI),

R₃—NH—(CH₂)ₘ—OH        (XVI)

c. To prepare a compound of the formula (III) in which R₂' is a group of the formula —(CH₂)ₘ—OH, an α,ω-dihaloalkyl compound of the formula (XVII)

Hal—(CH₂)ₙ—Hal        (XVII)

is reacted with an aminoalcohol of the formula (XVI).

d. To prepare a compound of the formula (III) in which m is equal to 4, a diamine of the formula (XII), is reacted with butyrolactone, and the obtained product is reduced.

A secondary amine of the formula (VII) is reacted with an ω-haloalkylchloride of the formula (XVIII),

Cl—(CH₂)ₙ—Hal        (XVIII)

wherein Hal is halogen, preferably bromine or iodine, and the resulting aminoalkyl chloride of the formula (XV) is converted into the desired compound of the formula (III) as described at (b) above.

Process variant (a) is performed as follows: In the first step a secondary amine of the formula (VII) is brought into an addition reaction with an acrylate of the formula (VIII). The addition proceeds in the absence of solvent, under stirring at room temperature. The resulting β-dialkylamino-propionate of the formula (IX) is then amidated with a primary amine of the formula (X). This reaction is performed preferably at elevated temperatures, such as at 100° C to 120° C, in the presence of a solvent, such as an alcohol or an aromatic hydrocarbon, particularly ethanol, under superatmospheric pressure, particularly about 5 to 8 atmospheres. The resulting β-dialkylaminopropionic amide of the formula (XI) is reduced to obtain a diamine of the formula (XII). The reduction is performed in an anhydrous inert solvent, preferably in an aliphatic or cycloaliphatic ether, such as diethyl ether, dioxane or tetrahydrofuran, with a complex metal hydride, preferably lithium aluminum hydride, as reducing agent. The product is isolated from the reaction mixture and purified, if necessary.

In the next step, the diamine of the formula (XII) is reacted with a haloalcohol of the formula (XIII). This reaction is performed in a solvent, preferably in an alcohol or aromatic hydrocarbon. Ethanol has proven to be a particularly preferred solvent. To bind the hydrogen halide liberated in the condensation, an acid binding agent, such as an alkali metal hydroxide or an alkali metal carbonate, is added to the reaction mixture. An excess of the amine reactant may also be used as the acid binding agent. The product is purified preferably by distillation.

The first step of the synthesis according to process variant (b) is performed in a solvent under heating. As the solvent, e.g. alcohols, aromatic hydrocarbons or lower ketones, preferably ethanol, benzene or acetone, can be used. According to a preferred method, the secondary amine of the formula (VII) is reacted with the haloalcohol of the formula (XIX) under stirring at refluxing temperature, in the presence of an acid binding agent, particularly an alkali metal hydroxide or alkali metal carbonate. An excess of the amine reactant can also serve as the acid binding agent. The obtained aminoalcohol of the formula (XIV) is purified preferably by distillation, and is then reacted with thionyl chloride. The reaction is performed at room temperature in the presence of a solvent, preferably a chlorinated aliphatic hydrocarbon, such as chloroform or carbon tetrachloride. The resulting aminoalkyl chloirde of the formula (XV) is isolated from the reaction mixture according to known techniques. In the last step of the synthesis, this aminoalkyl chloride is reacted with the appropriate aminoalcohol of the formula (XVI) in a solvent, preferably in ethanol, in the presence of an acid binding agent, preferably anhydrous potassium carbonate. The reaction is performed by stirring the mixture at refluxing temperature.

According to process variant (c) an α,ω-dihaloalkyl compound of the formula (XVII) is reacted with an aminoalcohol of the formula (XVI) in a solvent, in the presence of an acid binding agent. The reaction is performed preferably in an alcohol, particularly in ethanol. As the acid binding agent, an alkali metal hydroxide or carbonate, preferably anhydrous potassium carbonate, is used. The reaction mixture is stirred and refluxed for about 10 to 15 hours.

In the first step of the synthesis according to process variant (d), butyrolactone is used in a slight excess, and the reaction mixture is refluxed for several hours. Thereafter the mixture is cooled, and the product is reduced. The reduction is performed in an anhydrous inert solvent, preferably in an aliphatic or cycloaliphatic ether, such as diethyl ether or tetrahydrofuran. As the reducing agent, a complex metal hydride, particularly lithium aluminum hydride, is used.

The first step of the synthesis according to process variant (e) is performed in a solvent. As the solvent, e.g. anhydrous aromatic hydrocarbons or aliphatic ethers, preferably benzene or ethyl ether, can be used. According to a preferred method a secondary amine of the formula (VII) is reacted in diethyl ether at room temperature, under stirring, with the appropriate Ω-haloalkyl chloride of the formula (XVIII). It is preferred to use an excess of the amine reactant as acid binding agent. The resulting aminoalkyl chloride of the formula (XV) is preferably purified by distillation, and treated subsequently as described above in connection with process variant (b).

The other starting substances, the preparation of which is not described here, are either known or can be prepared according to known processes.

The compounds of the formula (I) and their salts of the formula (II) possess valuable pharmacological properties. These compounds primarily have cholinolytic and bronchospasmolytic effects, and can be used in therapy as medicines.

In contrast to the known substances with cholinolytic effects (e.g. atropine), the new compounds do not affect the central nervous system. The effective dosages of the new compounds, unlike the known bronchospasmolytic agents (such as isoprenaline), do not affect cardiac activity either.

Some diaminoalcohols with related structures have already been described in the literature, but these compounds are either pharmacologically inactive (Chem. Abstr. 50, 19143g, Chem. Abstr. 72, 54641g), or possess such other effects, e.g. coronary dilatating (Chem.

Abstr. 61, 11995b) or ganglion-blocking activities (Chem. Abstr. 53, 7208a), that do not permit conclusions to their possible cholinolytic or bronchospasmolytic activities.

The pharmacological tests were performed with the following compounds of the general formula (I):

A: 3-(N-methyl-N-[3-dimethylaminopropyl])-aminopropyl-xanthene-9-carboxylate dimethoiodide,
B: 3-(N-methyl-N-[3-methyl-ethyl-aminopropyl])-aminopropyl-xanthene-9-carboxylate dimethoiodide;
C: 3-(N-methyl-N-[3-pyrrolidinopropyl])-aminopropyl-xanthene-9-carboxylate dimethoiodide;
D: 3-(N-methyl-N-[2-diethylaminoethyl])-aminopropyl-xanthene-9-carboxylate dimethoiodide;
E: 2-(N-methyl-N-[2-diethylaminoethyl])-aminoethyl-xanthene-9-carboxylate dimethoiodide;
F: 4-(N-methyl-N-[3-diethylaminopropyl])-aminobutyl-xanthene-9-carboxylate dimethoiodide;
G: 3-(N-ethyl-N-[3-diethylaminopropyl])-aminopropyl-xanthene-9-carboxylate dimethoiodide;
H: 3-(N-methyl-N-[3-dipropylaminopropyl])-aminopropyl-xanthene-9-carboxylate dimethoiodide;
I: 3-(N-methyl-N-[3-diethylaminopropyl])-aminopropyl-xanthene-9-carboxylate diethoiodide;
K: 3-(N-methyl-N-[3-diethylaminopropyl])-aminopropyl-xanthene-9-carboxylate dimethoiodide;
L: N,N'-dimethyl-N,N'-bis(3-xanthene-9-carbonyloxypropyl)-1,3-diaminopropane dimethoiodide.

As reference substances, atropine (a widely used cholinolytic and bronchospasmolytic agent) and theophylline (a substance possessing primarily bronchospasmolytic effects) were used. In these tests, the $ED_{50}$ values of the individual compounds were determined, and the activities of these compounds were calculated as percentages of the activity of atropine. The results of the tests are summarized in Table 1. Notes to Table 1:

I = Determination of acetylcholine antagonism:
1. tests performed on mice by measuring the diameter of pupil (Arch. Exp. Path. Pharm. 168, 307 [1932]),
2. tests performed on isolated guinea pig intestines (Pflugers Arch. 102, 123 [1904]).

II = Determination of bronchospasmolytic effects:
3. tests performed on isolated guinea pig trachea (J. Pharm. Pharmac. 22, 46 [1970]),
4. tests performed by measuring the respiratory resistance of guinea pigs (Arch. Exp. Path. Pharmac. 195, 71 [1940]),
5. tests performed by measuring the antagonism against a bronchial spasm of guinea pigs induced by acetylcholine inhalation (Arzneimittelforschung 23, 854 [1973]).

Table 1

| Compound | I (1) | I (2) | II (3) | II (4) | II (5) |
|---|---|---|---|---|---|
| A | 42 | 3.1 | 11 | 35 | 42 |
| B | 95 | 7.2 | 17 | 75 | 61 |
| C | 89 | 5.6 | 15 | 34 | 57 |
| D | 2.9 | 0.31 | 0.12 | 0.21 | 6.2 |
| E | 3.7 | 0.29 | 0.21 | 0.17 | 7.1 |
| F | 27 | 1.8 | 0.97 | 22 | 15 |
| G | 45 | 2.9 | 9.6 | 17 | 44 |
| H | 15 | 1.5 | 5.7 | 19 | 11 |
| I | 101 | 6.2 | 12.3 | 65 | 63 |
| K | 311 | 25 | 60 | 270 | 214 |
| L | 305 | 107 | 50 | 157 | 131 |
| Atropine | 100 | 100 | 100 | 100 | 100 |
| Theophylline | — | $3 \times 10^{-4}$ | $10^{-3}$ | $7 \times 10^{-3}$ | $1.2 \times 10^{-1}$ |

As appears from the data of Table 1, the cholinolytic effects of the new compounds measured on mice pupils approach to, or sometimes even surpass, that of atropine. In this respect compounds K and L proved to be particularly valuable. The bronchospasmolytic effects of the new compounds exceed that of theophylline significantly in all of the cases examined.

The compounds according to the invention have shown no central nervous effects and harmful effects on cardiac action (which are characteristic and well-known side-effects of atropine and theophylline) in pharmacological tests. Moreover, they have shown none of the characteristic harmful side-effects of 3,4-dioxyphenyl-propylaminoethanol (isoprenaline), the most active of the known bronchodilatating agents, i.e., tachycardia or coronaria insufficiency appearing mainly after subcutaneous administration.

Consequently, the new compounds according to the invention can be used in therapy primarily as bronchospasmolytic agents. The major advantage of these compounds is the complete absence of harmful side-effects. Moreover, some of the new compounds are superior to hitherto known bronchospasmolytics even in the absolute value of activity.

In the human therapy, as well as for veterinary purposes in the treatment of larger mammals, the new compounds can be administered generally in a daily dosage of about 0.5 to 5 mg., preferably 1 to 3 mg. This amount can be added optionally in subdivided form (e.g. in two or more dosages of 0.4 to 1 mg.) or in the form of sustained-release compositions. The actual dosage depends primarily on the mode of administration, the condition of the patient and the severity of the disorder to be treated.

The compounds according to the invention can be converted into pharmaceutical compositions suitable for oral, parenteral, rectal administration or inhalation, such as tablets, coated tablets, capsules, injections, suspensions, syrups, suppositories, aerosols, sprays, etc. The pharmaceutical compositions are prepared by admixing the active ingredients with one or more conventional inert, non-toxic, solid or liquid pharmaceutical carrier and/or auxiliary agent. As carriers e.g. water, gelatine, lactose, starch, talc, magnesium stearate, vaseline, gum arabic, vegetable oils, polyalkylene glycols, etc. can be used. The pharmaceutical compositions may contain conventional auxiliary agents, such as preserving, stabilizing, wetting or emulsifying agents, buffers, flavoring agents, etc.

The invention is elucidated in detail in the following non-limiting Examples.

EXAMPLE 1

3-(N-Methyl-N-[3-diethylaminopropyl])-aminopropyl-xanthene-9-carboxylate dimethoiodide a. Methyl-(3-diethylminopropyl)-amine A mixture of 120 g. of freshly distilled methyl acrylate and 105 g. of diethylamine is stirred at room temperature for 30 hours. The obtained product, weighing 150 g., is distilled (b.p.: 95°–97° C/30 mmHg., $n_D^{20} = 1.4268$), the distillate is admixed with 100 ml. of a 33% ethanol solution of methylamine and the mixture is shaken in an autoclave at 100° C for 15 hours. The obtained 71 g. of β-diethylaminopropionic acid methylamide (b.p.: 160°–165° C/30 mmHg., $n_D^{22} = 1.4600$) are reduced with 14 g. of lithium aluminum hydride in 300 ml. of anhydrous diethyl ether, under stirring at reflux temperature. When the reaction has terminated the mixture is decomposed with aqueous sodium hydroxide solution and the solvent is evaporated. The residue is subjected to fractional distillation. 30 g. of methyl-(3-diethylaminopropyl)-amine are obtained; b.p.: 85°–92° C/30 mmHg., $n_D^{20}$ = 1.4383.

b.
3-(N-Methyl-N-[3-diethylaminopropyl])-aminopropanol 20 g. of anhydrous potassium carbonate are added to a solution of 15 g. of 1-chloro-propane-3-ol and 21.5 g. of methyl-(3-diethylaminopropyl)-amine in 120 ml. of anhydrous ethanol, and the mixture is stirred and refluxed for 30 hours. The reaction mixture is allowed to cool, filtered, and the filtrate is evaporated. The residue is distilled. 23 g. of 3-(N-methyl-N-[3-diethylaminopropyl])-aminopropanol are obtained; b.p.: 145°–146° C/14 mmHg, $n_D^{20}$ = 1.4608.

The following compounds can be prepared in a manner analogous to that described above:

5-(N-methyl-N-[3-diethylaminopropyl])-aminopentanol; b.p.: 125°–127° C/2 mmHg, $n_D^{20}$ = 1.4645, and
2-(N-methyl-N-[3-diethylaminopropyl])-aminoethanol; b.p.: 124°–126° C/8 mmHg.

c.
3-(N-Methyl-N-[3-diethylaminopropyl])-aminopropyl-xanthene-9-carboxylate dimethoiodide A solution of 5.2 g. of 3-(N-methyl-N-[3-diethylaminopropyl])-aminopropanol in 20 ml. of anhydrous benzene is added dropwise to a cooled solution of 6.5 g. of xanthene-9-carboxylic chloride in 20 ml. of benzene. The reaction mixture is refluxed for 2 hours, thereafter it is allowed to cool, and washed with a 20% aqueous sodium hydroxide solution. The benzene phase is dried, and the solvent is evaporated. 11 g. of 3-(N-methyl-N-[3-diethylaminopropyl])-aminopropyl-xanthene-9-carboxylate are obtained.

3 g. of the above base are dissolved in 20 ml. of a 2:1 mixture of acetone and ethanol, and 2.2 g. of methyl iodide are added to the mixture. The mixture is kept under gentle boiling for 20 minutes, thereafter it is allowed to stand under cooling. The separated crystals are filtered off and recrystallized from aqueous ethanol. 3.5 g. of the dimethoiodide are obtained; m.p.: 151°–152° C.

The hydrochloride can be prepared as follows:

2 g. of the free base are dissolved in 15 ml. of anhydrous ethanol, and dry hydrogen chloride is introduced into the solution under cooling. The separated crystals are filtered off and recrystallized from aqueous ethanol. The dihydrochloride melts at 173°–174° C.

Similarly can be prepared the following compounds:

3-(N-methyl-[3-diethylaminopropyl])-aminopropyl-xanthene-9-carboxylate diethoiodide, m.p.: 142°–143° C,
5-(N-methyl-N-[3-diethylaminopropyl])-aminopentyl-xanthene-9-carboxylate dimethoiodide, m.p.: 147°–148° C, and
2-(N-methyl-N-[3-diethylaminopropyl])-aminoethyl-xanthene-9-carboxylate dimethoiodide, m.p.: 189°–190° C.

EXAMPLE 2

3-(N-Methyl-N-[3-dipropylaminopropyl])-aminopropyl-xanthene-9-carboxylate dimethoiodide a.
3-(N-Methyl-N-[3-dipropylaminopropyl])-aminopropanol A solution of 70 ml. of dipropylamine and 24 ml. of 3-chloropropanol in 100 ml. of anhydrous benzene is refluxed for 15 hours. The solution is allowed to cool, the separated crystals are filtered off, the filtrate is evaporated, and the residue is distilled. 32 g. of the resulting 3-dipropylaminopropanol are dissolved in 110 ml. of chloroform, and 17.5 ml. of thionyl chloride are added dropwise to the stirred solution. The mixture is stirred at room temperature for additional 24 hours. The reaction mixture is extracted with cold 20% aqueous sodium hydroxide solution, the chloroform phase is dried, evaporated, and the residue is distilled. 30 g. of the resulting 3-dipropylaminopropylchloride and 17 g. or 3-methylaminopropanol are dissolved in 150 ml. of anhydrous ethanol. 35 g. of anhydrous potassium carbonate are added to the solution, and the mixture is stirred and refluxed for 24 hours. The reaction mixture is allowed to cool, filtered, and the filtrate is evaporated. The residue is distilled. 30 g. of 3-(N-methyl-N-[3-dipropylaminopropyl])-aminopropanol are obtained; b.p.: 111°–112° C/5 mmHg, $n_D^{20}$ = 1.4600.

Similarly can be prepared the following compounds:

2-(N-methyl-N-[2-diethylaminoethyl])-aminoethanol, b.p.: 136°–138° C/30 mmHg,
3-(N-methyl-N-[3-diethylaminoethyl])-aminopropanol, b.p.: 142°–144° C/30 mmHg,
2-(N-methyl-N-[2-dimethylaminoethyl])-aminoethanol, b.p.: 85°–88° C/30 mmHg, and
2-(N-methyl-N-[3-methyl-ethylaminopropyl])-aminopropanol, b.p.: 118°–120° C/25 mmHg, $n_D^{20}$ = 1.4585.

b.
3-(N-Methyl-N-[3-dipropylminopropyl])-aminopropyl-xanthene-9-carboxylate dimethoiodide One proceeds as described in step (c) of Example 1 with the difference that 3-(N-methyl-N-[3-dipropylaminopropyl])-aminopropanol is used as starting substance. The dimethoiodide melts at 175°–176° C.

The following compounds are prepared similarly:

2-(N-methyl-N-[2-diethylaminoethyl])-aminoethyl-xanthene-9-carboxylate dimethoiodide, m.p.: 199°–200° C,
3-(N-methyl-N-[2-diethylaminoethyl])-aminopropyl-xanthene-9-carboxylate dimethoiodide, m.p.: 189°–190° C,
2-(N-methyl-N-[2-dimethylaminoethyl])-aminoethyl-xanthene-9-carboxylate dimethoiodide, m.p.: 217°–218° C, and
3-(N-methyl-N-[3-methyl-ethylaminopropyl])-aminopropyl-xanthene-9-carboxylate dimethoiodide, m.p.: 176°–178° C.

EXAMPLE 3

N,N'-Dimethyl-N,N'-bis(3-xanthen-9-carbonyloxypropyl)-1,3-diaminopropane dimethoiodide a.

N,N'-Dimethyl-N,N'-bis(3-hydroxypropyl)-1,3-diaminopropane 15 g. of anhydrous potassium carbonate are added to a solution of 9 g. of 3-methylaminopropanol and 10 g. of 1,3-dibromopropane in 100 ml. of ethanol, and the reaction mixture is stirred and refluxed for 24 hours. The mixture is allowed to cool, filtered, the filtrate is evaporated, and the residue is distilled. 6 g. of N,N'-dimethyl-N,N'-bis(3-hydroxypropyl)-1,3-diaminopropane are obtained; b.p.: 150°–154° C/2 mmHg, $n_D^{20} = 1.4793$.

b.

N,N'-Dimethyl-N,N'-bis(3-xanthene-9-carbonyloxypropyl)-1,3-diaminopropane dimethoiodide The diol obtained in step (a) above is treated as described in step (c) of Example 1. The obtained dimethoiodide melts at 194°–195° C.

EXAMPLE 4

4-(N-Methyl-N-[3-diethylaminopropyl])-aminobutyl-xanthene-9-carboxylate dimethoiodide a.

4-(N-Methyl-N-[3-diethylaminopropyl])-aminobutanol

A mixture of 20 g. of methyl-(3-diethylamino)-propylamine, prepared as described in step (a) of Example 1, and 12 g. of butyrolactone is refluxed for 24 hours. Thereafter 200 ml. of dry diethyl ether and 4.7 g. of lithium aluminum hydride are added to the mixture, and the condensate is reduced. When the reaction has terminated the solution is decomposed with aqueous sodium hydroxide solution, the etheric phase is separated, dried, and the solvent is evaporated. The residue is distilled. 12 g. of 4-(N-methyl-N-[3-diethylaminopropyl])-aminobutanol are obtained; b.p.: 123°–125° C/4 mmHg, $n_D^{20} = 1.4614$.

b.

4-(N-Methyl-N-[3-diethylaminopropyl])-aminobutyl-xanthene-9-carboxylate diemthoiodide The product obtained as described in step (a) above is treated as described in step (c) of Example 1. The obtained dimethoiodide melts at 149°–151° C.

EXAMPLE 5

3-(N-Ethyl-N-[3-diethylaminopropyl])-aminopropyl-xanthene-9-carboxylate dimethoiodide a.

3-(N-Ethyl-N-[3-diethylaminopropyl])-aminopropanol

A solution of 103 ml. of diethylamine and 78 g. of 3-bromopropylchloride in 100 ml. of anhydrous diethyl ether is stirred and refluxed for 10 hours. The mixture is allowed to cool, filtered, and the filtrate is evaporated. The residue is distilled. 14 g. of the resulting 3-diethylaminopropyl chloride and 9 g. of 3-ethylaminopropanol are dissolved in 40 ml. of anhydrous ethanol, 15 g. of anhydrous potassium carbonate are added, and the mixture is stirred and refluxed for 25 hours. The mixture is allowed to cool, is filtered, and the filtrate is evaporated. The residue is distilled. 7 g. of 3-(N-ethyl-N-[3-diethylaminopropyl])-aminopropanol are obtained; b.p.: 118°–120° C/6 mmHg, $n_D^{20} = 1.4636$.

The following compounds can be prepared similarly:

2-(N-methyl-N-[3-pyrrolidinopropyl])-aminoethanol, b.p.: 145°–150° C/30 mmHg., 3-(N-methyl-N-[3-pyrrolidinopropyl])-aminopropanol, b.p.: 156°–160° C/30 mmHg., and 3-(N-methyl-N-[3-dimethylaminopropyl])-aminpropanol, b.p.: 88°–90° C/7 mmHg., $n_D^{20} = 1.4612$.

b.

3-(N-Ethyl-N-[3-diethylaminopropyl])-aminopropyl-xanthene-9-carboxylate dimethoiodide 3-(N-Ethyl-N-[3-diethylaminopropyl])-aminopropanol, prepared as described in point (a) above, is treated as described in step (c) of Example 1 to obtain 3-N-ethyl-N-[3-diethylaminopropyl])-aminopropyl-xanthene-9-carboxylate dimethoiodide. The product melts at 154°–156° C.

The following compounds are prepared similarly:

2-(N-methyl-N-[3-pyrrolidinopropyl])-aminoethyl-xanthene-9-carboxylate dimethoiodide, m.p.: 218°–219° C, 3-(N-methyl-N-[3-pyrrolidinopropyl])-aminopropyl-xanthene-9-carboxylate dimethoiodide, m.p.: 180°–181° C, and 3-(N-methyl-N-[3-dimethylaminopropyl])-aminopropyl-xanthene-9-carboxylate dimethoiodide, m.p.: 193°–195° C.

EXAMPLE 6

3-(N-Methyl-N-[3-dipropylaminopropyl])-aminopropyl-xanthene-9-carboxylate dimethoiodide 0.5 ml. of a sodium methoxide solution are added to a heated mixture of 5.7 g. of 3-(N-methyl-N-[3-dipropylaminopropyl])-aminopropanol (prepared as described in step (a) of Example 2) and 12 g. of methyl xanthene-9-carboxylate, and the reaction mixture is maintained at 100° C for 1 hour. During this period the methanol formed is removed by distillation. The reaction mixture is allowed to cool, diluted with 50 ml. of benzene, and extracted with 25 ml. of 5% aqueous hydrochloric acid. The aqueous solution is decolorized with charcoal, filtered, and rendered alkaline with 30 ml. of a cold 5% aqueous sodium hydroxide solution. The aqueous-alkaline solution is extracted with ether. The etheric phase is dried, and the solvent is evaporated. The obtained 11 g. of 3-(N-methyl-N-[3-dipropylaminopropyl])-aminopropyl-xanthene-9-carboxylate is converted into its dimethoiodide as described in step (c) of Example 1. The quaternary salt melts at 175°–176° C.

What is claim is:

1. A xanthene-9-carboxylate of the formula (I), (I)

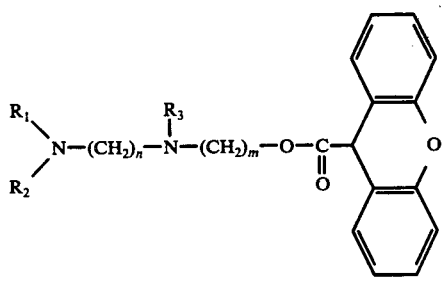

wherein

R₁ and R₃ are the same or different and each is lower alkyl,

R₂ is lower alkyl and n and m each are integers of 2 to 5, or a pharmaceutically effective salt thereof.

2. A compound as defined in claim 1 which consists of 3-(N-methyl-N-[3-diethylaminopropyl])-aminopropyl-xanthene-9-carboxylate dimethoiodide.

3. A compound as defined in claim 1 which consists of 3-(N-methyl-N-[3-diethylaminopropyl])-aminopropyl-xanthene-9-carboxylate diethoiodide.

4. A pharmaceutically effective salt of the formula (II), (II)

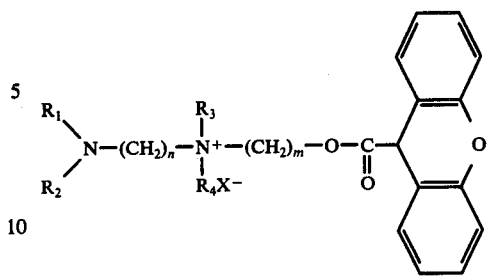

wherein $R_1$, $R_2$, and $R_3$, are each lower alkyl, m and n each are integers of 2 to 5, $R_4$ is hydrogen or lower alkyl, and X is an organic or mineral acid residue.

5. A pharmaceutical composition with cholinolytic and bronchospasmolytic effect containing as active ingredient a compound as defined in claim 1 of the formula (I), along with a carrier of diluent.

6. A pharmaceutical composition with cholinolytic and bronchospasmolytic effect as defined in claim 5 wherein 3-(N-methyl-N-[3-diethylaminopropyl])-aminopropyl-xanthene-9-carboxylate dimethoiodide is said active ingredient.

7. A method for the treatment of bronchial spasms, comprising administering an effective amount of a compound as defined in claim 1 of the formula (I).

8. A method as claimed in claim 7 wherein said compound of the formula (I) is administered in a daily dosage of 0.5 to 5 mg.

9. A method as claimed in claim 8 wherein said compound of the formula (I) is administered in a daily dosage of 1 to 3 mg.

* * * * *